United States Patent
Ishii

(10) Patent No.: US 10,157,176 B2
(45) Date of Patent: Dec. 18, 2018

(54) INFORMATION PROCESSING APPARATUS AND DISPLAY METHOD

(71) Applicant: FUJITSU LIMITED, Kawasaki (JP)

(72) Inventor: Masamichi Ishii, Saitama (JP)

(73) Assignee: FUJITSU LIMITED, Kawasaki (JP)

( * ) Notice: Subject to any disclaimer, the term of this patent is extended or adjusted under 35 U.S.C. 154(b) by 26 days.

(21) Appl. No.: 15/414,879

(22) Filed: Jan. 25, 2017

(65) Prior Publication Data
US 2017/0220549 A1    Aug. 3, 2017

(30) Foreign Application Priority Data

Jan. 28, 2016 (JP) .................................. 2016-014909

(51) Int. Cl.
| | | |
|---|---|---|
| *G06F 17/24* | (2006.01) | |
| *G06F 17/27* | (2006.01) | |
| *G06F 3/0482* | (2013.01) | |
| *G16H 10/60* | (2018.01) | |

(52) U.S. Cl.
CPC .......... *G06F 17/276* (2013.01); *G06F 3/0482* (2013.01); *G06F 17/241* (2013.01); *G16H 10/60* (2018.01)

(58) Field of Classification Search
CPC ..................................................... G06F 17/276
USPC ......................................................... 715/271
See application file for complete search history.

(56) References Cited

U.S. PATENT DOCUMENTS

| | | | | |
|---|---|---|---|---|
| 8,498,999 | B1 * | 7/2013 | Bhalotia | G06F 17/3064 707/767 |
| 2006/0031096 | A1 * | 2/2006 | Buttner | G06F 17/24 705/2 |
| 2007/0174045 | A1 * | 7/2007 | Kao | G06F 17/278 704/4 |
| 2009/0037474 | A1 * | 2/2009 | Faulkner | G06F 17/3053 |

(Continued)

FOREIGN PATENT DOCUMENTS

| | | |
|---|---|---|
| JP | 8-339373 A | 12/1996 |
| JP | 2009-244950 A | 10/2009 |

OTHER PUBLICATIONS

Meystre, Stéphane M., Guergana K. Savova, Karin C. Kipper-Schuler, and John F. Hurdle. "Extracting information from textual documents in the electronic health record: a review of recent research." Yearbook of medical informatics 17, No. 01 (2008): 128-144. (Year: 2008).*

*Primary Examiner* — Frank D Mills
(74) *Attorney, Agent, or Firm* — Westerman, Hattori, Daniels & Adrian, LLP

(57) ABSTRACT

A method includes accepting an input of text from an input device, detecting a string of characters from the text, the string of characters corresponding to an abbreviation, the abbreviation corresponding to a plurality of phrases, the plurality of phrases having different meanings respectively, generating the plurality of phrases for display in an interactive display window on a display device, the plurality of phrases being generated from a database storing correspondence information between the string of characters and the plurality of phrases, and displaying the plurality of phrases on the interactive display window as candidates for an appropriate phrase corresponding to the abbreviation in the text, the interactive display window being configured to (Continued)

enable a user to select the appropriate phrase from among the plurality of phrases.

15 Claims, 13 Drawing Sheets

(56) References Cited

U.S. PATENT DOCUMENTS

| | | | |
|---|---|---|---|
| 2009/0248671 A1 | 10/2009 | Maruyama et al. | |
| 2014/0282238 A1* | 9/2014 | Dart .................... | G06F 3/04817 715/810 |
| 2015/0066480 A1* | 3/2015 | Endo ................... | G06F 17/2765 704/9 |

* cited by examiner

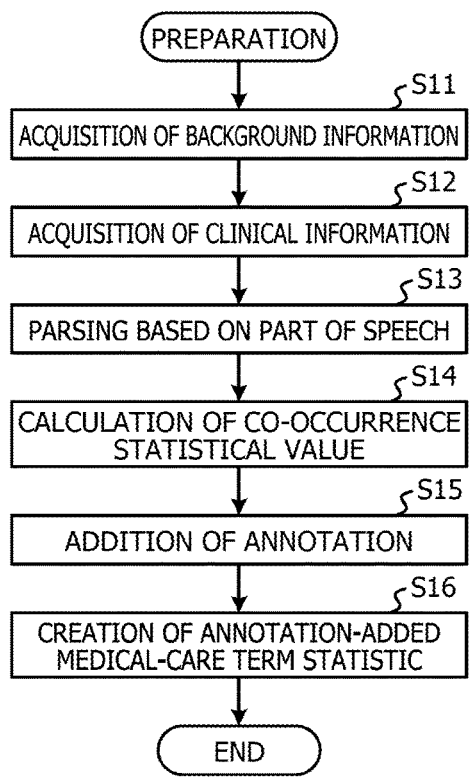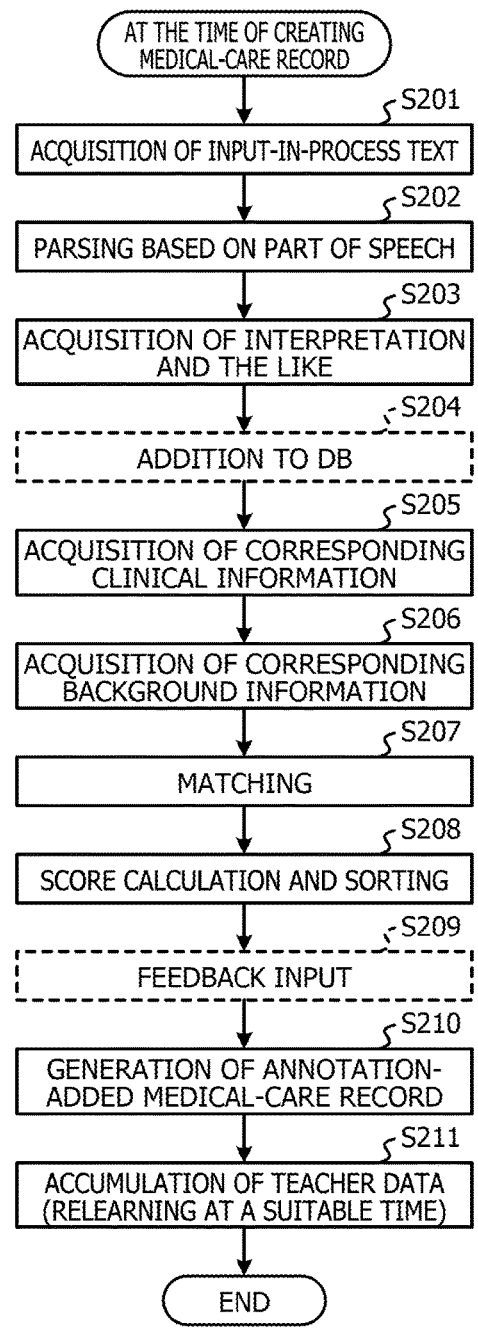

FIG. 6A

IN CLINICAL RECORD INSPECTION, INSERTION INTO LEFT PULMONARY ARTERY IS PERFORMED, DRAWN PRESSURE CURVE UP TO RIGHT VENTRICLE IS FORMED, CHANGE IN PRESSURE INCREASE AND PRESSURE WAVEFORM IN THE VICINITY OF PULMONARY VALVE OF PULMONARY ARTERY MAIN TUBE PORTION IS RECOGNIZED, AND DIAGNOSIS OF PDA COMBINED WITH ASD IS MADE. ←— 311

FIG. 6B

[TERM] ASD     (WHICH IS USED, BY PERSON IN CHARGE OF PERFORMING INPUTTING TO MEAN "Aortic Septal Defect")

FIG. 6C

[EXTRACTION DATA #1]
[MEDICAL-TERM DICTIONARY] ASD    autosensitized dermatitis
(DATA ATTRIBUTE) MEDICAL-CARE DEPARTMENT: DERMATOLOGY [RECE ELECTRONIC CODE: 19 DERMATOLOGY]
[MEDICAL-TERM DICTIONARY] ASD    applicator skin distance
(DATA ATTRIBUTE) MEDICAL-CARE DEPARTMENT: DERMATOLOGY [RECE ELECTRONIC CODE: 19 DERMATOLOGY]
[MEDICAL-TERM DICTIONARY] ASD    aortic septal defect
(DATA ATTRIBUTE) MEDICAL-CARE DEPARTMENT: CHILDHOOD CARDIAC SURGERY [RECE ELECTRONIC CODE: 162 CARDIAC SURGERY]
[MEDICAL-TERM DICTIONARY] ASD    atrial septal defect
(DATA ATTRIBUTE) MEDICAL-CARE DEPARTMENT: CARDIOLOGY [RECE ELECTRONIC CODE: 164 CARDIOVASCULAR SURGERY]

FIG. 7A

[EXTRACTION DATA #2]
[CLINICAL INFORMATION]
DISEASE NAME: AORTA PULMONARY ARTERY TRUNK SEPTAL DEFECT [icd10:Q21.4], CARDIAC FAILURE, BRONCHITIS
SYMPTOM: DYSPNEA, BREATHLESSNESS
CHECKUP ITEM: ECHOCARDIOGRAM (SUPERSONIC RAYS) CHECKUP
MEDICATION: DIURETIC (SUMMARY DISEASE NAME: CARDIAC FAILURE)

[EXTRACTION DATA #3]
[BACKGROUND INFORMATION: USER] CATEGORY OF OCCUPATION: DOCTOR, MEDICAL SPECIALIST: CHILD SURGERY
[BACKGROUND INFORMATION: PATIENT] AGE: 10 YEARS OLD, MEDICAL CHECKUP FOR OUTPATIENT: CHILDHOOD CARDIAC SURGERY
[BACKGROUND INFORMATION: ENVIRONMENT] INPUTTING PLACE: BOOTH 11 FOR OUTPATIENT [RESERVED SPOT: CHILDHOOD CARDIAC SURGERY]
STATEMENT FORM: PROGRESS NOTE

[MEDICAL-TERM DICTIONARY] ASD    autosensitized dermatitis
(DATA ATTRIBUTE) MEDICAL-CARE DEPARTMENT: DERMATOLOGY [RECE ELECTRONIC CODE: 19 DERMATOLOGY]
→ NO CONSISTENCE

[MEDICAL-TERM DICTIONARY] ASD    applicator skin distance
(DATA ATTRIBUTE) MEDICAL-CARE DEPARTMENT: DERMATOLOGY [RECE ELECTRONIC CODE: 19 DERMATOLOGY]
→ NO CONSISTENCE

[MEDICAL-TERM DICTIONARY] ASD    aortic septal defect
(DATA ATTRIBUTE) MEDICAL-CARE DEPARTMENT: CHILDHOOD CARDIAC SURGERY [RECE ELECTRONIC CODE: 162 CARDIAC SURGERY]
→[EXTRACTION DATA #2] "AORTA" AND "SEPTAL DEFECT " OF DISEASE NAME: AORTA PULMONARY ARTERY TRUNK SEPTAL DEFECT ARE PARTIALLY CONSISTENT
→[EXTRACTION DATA #3] "CHILD" AND "SURGERY" OF MEDICAL SPECIALIST: CHILD SURGERY ARE PARTIALLY CONSISTENT
→[EXTRACTION DATA #3] PATIENT: MEDICAL CHECKUP FOR OUTPATIENT: "CHILDHOOD CARDIAC SURGERY" IS COMPLETELY CONSISTENT
→[EXTRACTION DATA #3] INPUTTING PLACE: BOOTH 11 FOR OUTPATIENT AND "CHILDHOOD CARDIAC SURGERY" ARE COMPLETELY CONSISTENT

[MEDICAL-TERM DICTIONARY] ASD    atrial septal defect
(DATA ATTRIBUTE) MEDICAL-CARE DEPARTMENT: CARDIOLOGY [RECE ELECTRONIC CODE: 164 CARDIOVASCULAR SURGERY]
→[EXTRACTION DATA #2] "CARDIAC" OF DISEASE NAME: CARDIAC FAILURE IS PARTIALLY CONSISTENT

FIG. 9

```
CO-OCCURRENCE STATISTIC OF NO-ANNOTATION CORPUS
 0.009 "ASD" AND "CHILD SURGERY"
 0.016 "ASD" AND "CHILDHOOD CARDIAC SURGERY"

CO-OCCURRENCE STATISTIC OF ANNOTATION CORPUS
 0.012 "ASD (aortic septal defect)" and "CHILD SURGERY"
 0.019 "ASD (aortic septal defect)" and "CHILDHOOD CARDIAC SURGERY"
 0.011 "ASD (aortic septal defect)" and "CARDIAC FAILURE"
```

FIG. 10A 0.000 [MEDICAL-TERM DICTIONARY] ASD    autosensitized dermatitis
(DATA ATTRIBUTE) MEDICAL-CARE DEPARTMENT: DERMATOLOGY [RECE ELECTRONIC CODE: 19 DERMATOLOGY]
0.000 [MEDICAL-TERM DICTIONARY] ASD    applicator skin distance
(DATA ATTRIBUTE) MEDICAL-CARE DEPARTMENT: DERMATOLOGY [RECE ELECTRONIC CODE: 19 DERMATOLOGY]
0.0413 [MEDICAL-TERM DICTIONARY] ASD    aortic septal defect
(DATA ATTRIBUTE) MEDICAL-CARE DEPARTMENT: CHILDHOOD CARDIAC SURGERY [RECE ELECTRONIC CODE: 162 CARDIAC SURGERY]
0.0033 [MEDICAL-TERM DICTIONARY] ASD    atrial septal defect
(DATA ATTRIBUTE) MEDICAL-CARE DEPARTMENT: CARDIOLOGY [RECE ELECTRONIC CODE: 164 CARDIOVASCULAR SURGERY]

SORTING IN ORDER OF DECREASING SCORE

FIG. 10B 0.0413 [MEDICAL-TERM DICTIONARY] ASD    aortic septal defect
(DATA ATTRIBUTE) MEDICAL-CARE DEPARTMENT: CHILDHOOD CARDIAC SURGERY [RECE ELECTRONIC CODE: 162 CARDIAC SURGERY]
0.0033 [MEDICAL-TERM DICTIONARY] ASD    atrial septal defect
(DATA ATTRIBUTE) MEDICAL-CARE DEPARTMENT: CARDIOLOGY [RECE ELECTRONIC CODE: 164 CARDIOVASCULAR SURGERY]
0.000 [MEDICAL-TERM DICTIONARY] ASD    autosen sitized dermatitis
(DATA ATTRIBUTE) MEDICAL-CARE DEPARTMENT: DERMATOLOGY [RECE ELECTRONIC CODE: 19 DERMATOLOGY]
0.000 [MEDICAL-TERM DICTIONARY] ASD    applicator skin distance
(DATA ATTRIBUTE) MEDICAL-CARE DEPARTMENT: DERMATOLOGY [RECE ELECTRONIC CODE: 19 DERMATOLOGY]

FIG. 11A

IN CLINICAL RECORD INSPECTION, INSERTION INTO LEFT PULMONARY ARTERY IS PERFORMED, DRAWN PRESSURE CURVE UP TO RIGHT VENTRICLE IS FORMED, CHANGE IN PRESSURE INCREASE AND PRESSURE WAVEFORM IN THE VICINITY OF PULMONARY VALVE OF PULMONARY ARTERY MAIN TUBE PORTION IS RECOGNIZED, AND DIAGNOSIS OF PDA COMBINED WITH *ASD* IS MADE.

FIG. 11B

IN CLINICAL RECORD INSPEC[
LEFT PULMONARY ARTERY I[
PRESSURE CURVE UP TO [
FORMED, CHANGE IN PRES[
PRESSURE WAVEFORM IN THE VICINITY OF
PULMONARY VALVE OF PULMONARY ARTERY MAIN
TUBE PORTION IS RECOGNIZED, AND DIAGNOSIS OF
PDA COMBINED WITH *ASD* IS MADE.

☑
☐ ASD  atrial septal defect
☐ ASD  autosen sitized dermatitis
☐ ASD  applicator skin distance
SELECT WITH ↑ AND ↓ AND CONFORM WITH Enter

FIG. 12A

```
<medicalTerm dictionary="" STANDARD MEDICAL TERM="aortic
septal defect">ASD</medicalTerm>
```

FIG. 12B

```
<mt item="aortic septal defect">ASD</mt>
```

FIG. 12C

```
...
COMBINE <mt item="aortic septal defect" cd="X16201">ASD</mt>
DIAGNOSE <mt item="Patent Ductus Arteri" cd="Q23456">PDA</mt>
...
```

INFORMATION PROCESSING APPARATUS AND DISPLAY METHOD

CROSS-REFERENCE TO RELATED APPLICATION

This application is based upon and claims the benefit of priority of the prior Japanese Patent Application No. 2016-014909, filed on Jan. 28, 2016, the entire contents of which are incorporated herein by reference.

FIELD

The embodiment discussed herein is related to a technology that controls assignment of attribution information.

BACKGROUND

In this day and age of information, the computerization of a clinical record created by a doctor has also been introduced. Such a clinical record is stored in a database by using a terminal apparatus and is allowed to be referred.

As one aspect of the use of the clinical information, there is an example in which prescribed disease cases are retrieved for consideration of characteristics of the disease or in which the incidence of occurrence of a prescribed disease is determined. In order to use the clinical information in such a way, medical terms such as disease names have to be standardized.

However a same abbreviation is often used as a term of different diseases. For example, a plurality of different definitions of the term "ASD" appear in a medical-term dictionary, as follows: ASD for autosensitized dermatitis; ASD for applicator skin distance; ASD for aortic septal defect; and ASD for atrial septal defect.

Furthermore, doctors and the like tend to use abbreviations frequently even in a statement in an electronic clinical record, since they tend to record information as only a reminder for themselves and think of the efficiency of entering a disease name in a clinical record.

On the other hand, an information classification technology is disclosed in Japanese Laid-open Patent Publication No. 2009-244950. Furthermore, a technology relating to a machine translation apparatus is disclosed in Japanese Laid-open Patent Publication No. 8-339373.

SUMMARY

According to an aspect of the invention, a method includes accepting an input of text from an input device, detecting a string of characters from the text, the string of characters corresponding to an abbreviation, the abbreviation corresponding to a plurality of phrases, the plurality of phrases having different meanings respectively, generating the plurality of phrases for display in an interactive display window on a display device, the plurality of phrases being generated from a database storing correspondence information between the string of characters and the plurality of phrases, and displaying the plurality of phrases on the interactive display window as candidates for an appropriate phrase corresponding to the abbreviation in the text, the interactive display window being configured to enable a user to select the appropriate phrase from among the plurality of phrases.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 3 is a diagram illustrating an example of data structures of various DBs and the like;

FIGS. 5A and 5B are flowcharts each illustrating an example of processing according to the embodiment;

FIGS. 6A, 6B, and 6C are diagrams each illustrating an example in which candidates for selection are extracted from a clinical record that is input, a term that is extracted, a medical-term dictionary;

FIGS. 7A and 7B are diagrams each illustrating an example in which clinical information and background information relating to an input are extracted;

FIG. 8 is a diagram illustrating an example of matching between pieces of extraction data;

FIG. 9 is a diagram illustrating an example of a co-occurrence statistic for every word;

FIGS. 10A and 10B are diagrams each illustrating an example of calculation of a score;

FIGS. 11A and 11B are diagrams each illustrating an example of a feedback input; and FIGS. 12A, 12B, and 12C are diagrams each illustrating an example of annotation information in the XML format.

DESCRIPTION OF EMBODIMENT

As described above, because an abbreviation and the like that have various meanings are included in a statement such as an electronic clinical record, there is a problem in that it is difficult to reuse the record.

Accordingly, one aspect of a technology that is disclosed according to an embodiment is to identify the meaning of a character string to be registered.

A suitable embodiment of the present disclosure will be described below. Description will be made on medical-care information such as the electronic clinical record, but there is no limitation on the information.

Constitution

Figure 1:
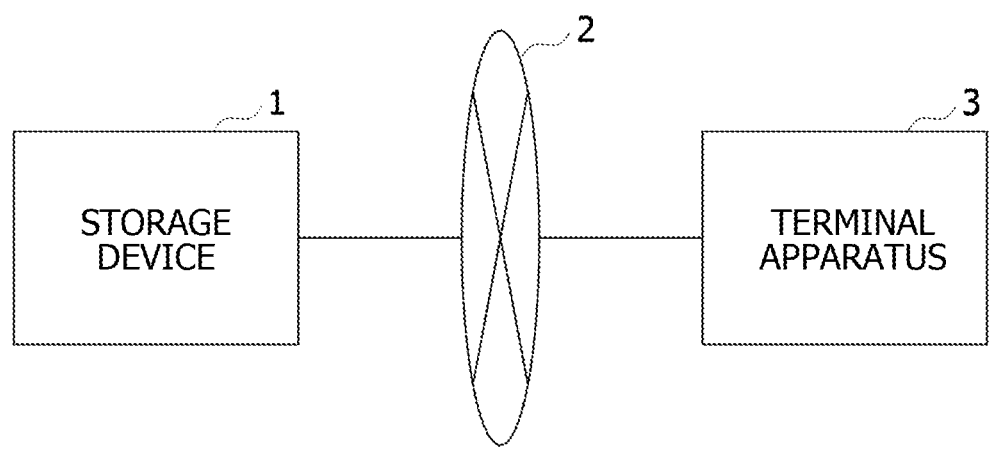
FIG. 1 is a diagram illustrating an example of a constitution of a system according to an embodiment.

FIG. 1 is a diagram illustrating an example of a constitution of a system according to an embodiment. In FIG. 1, a storage device 1 in which the medical-care information, such as the electronic clinical record, is stored or retained, is connected to a network 2, such as a Local Area Network (LAN) or a Wide Area Network (WAN), and it is possible that a terminal apparatus (an information processing apparatus) 3 that is used by a person such as a doctor is connected to the storage device 1 through the network 2.

Figure 2:
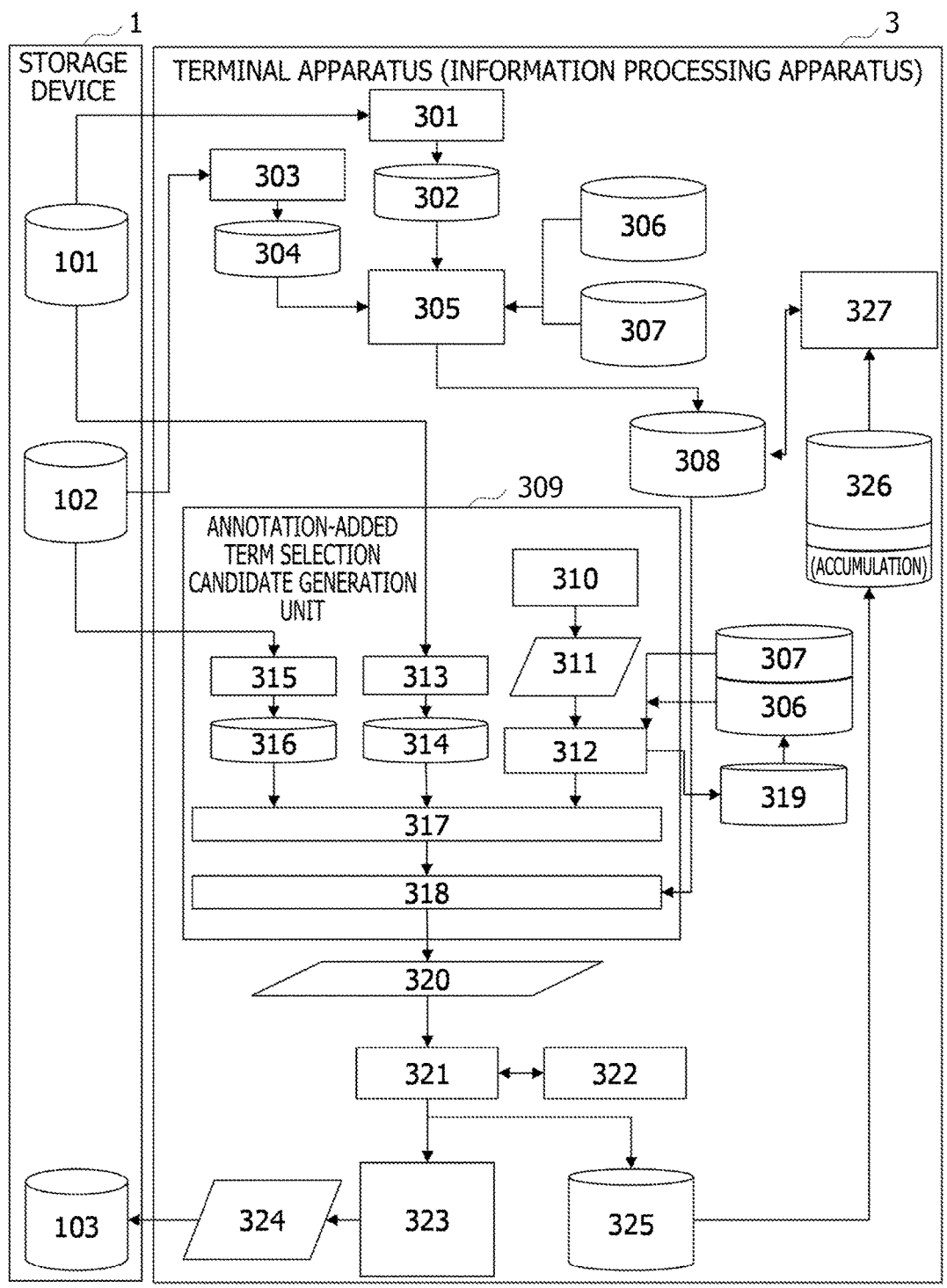
FIG. 2 is a diagram illustrating an example of a functional constitution relating to information processing.
Figure 3:
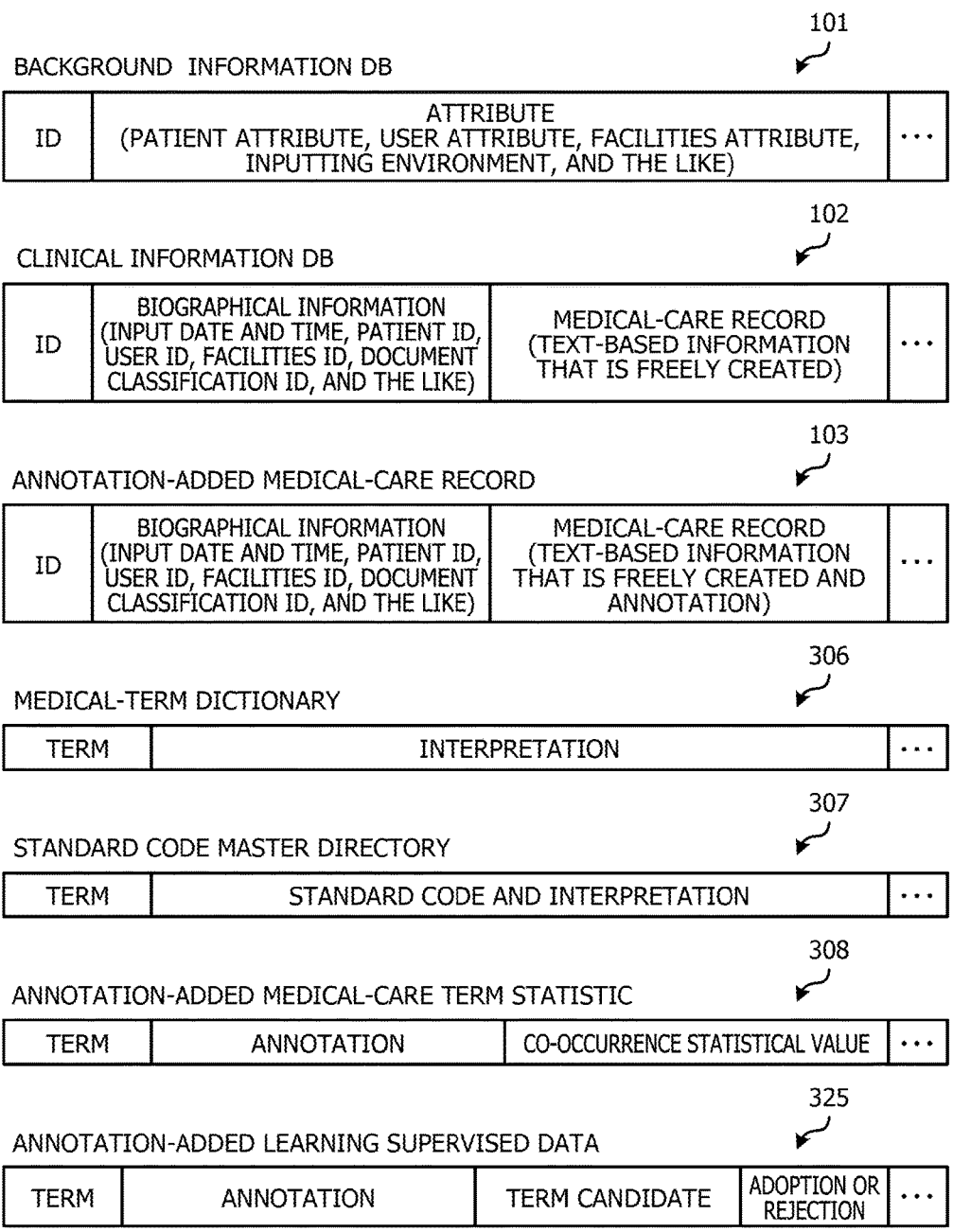

FIG. 2 is a diagram illustrating an example of a functional constitution relating to information processing. In FIG. 2, a background information DB 101 and a clinical information DB 102, and an annotation-added medical-care record 103 are included in the storage device 1. As illustrated in FIG. 3, a patient attribute, a user attribute, a facilities attribute, an inputting environment, and the like are stored, as attributes that are associated with a unique ID, in the background information DB 101. A full name, an address, sex, age, and a medical history (a disease name, allergy, and the like) of a patient, a result of medical examination by interview (lifestyle habits such as smoking and alcohol drinking), and the like are included in the patient attribute. Moreover, the patient is identified by a patient ID. A category of occupation (a doctor, a nurse, a medical check-up engineer, a carer, or the like) in which the user who performs information input is engaged, a department (a medical-care department) to which the user who performs the information input belongs, a medical specialist certificate that the user who performs the information input has, and the like are included in the user attribute. Moreover, the user is identified by a user ID. A medical examination place, a terminal apparatus-installed department (an outpatient medical examination room, a ward nurse center, a medical office, medical check-up, working from home, or the like), and the like where the information input is performed are included in the facilities attribute. Moreover, the facilities are identified by a facilities ID. A document classification (a progress annotation, a discharge-from-hospital summary, a nurse's record, a progress table, and the like), and the like that is a target into which the information is input are included in the inputting environment. Moreover, the document classification is identified by a document classification ID.

As illustrated in FIG. 3, biographical information (an input date and time, the patient ID, the user ID, the facilities ID, the document classification ID, and the like) and a medical-care record (text-based information that is freely created), which are associated with a unique ID, are included in the clinical information DB 102. As illustrated in FIG. 3, the biographical information (the input data and time, the patient ID, the user ID, the facilities ID, the document classification ID, and the like) and the medical-care record (text-based information that is freely created and annotations), which are associated with a unique ID, are included in the annotation-added medical-care record 103. The annotation-added medical-care record 103 is different from the clinical information DB 102 in that the annotations are added to the medical-care record, and is substantially the same as clinical information. The clinical information DB 102 is one in which the clinical information that is available before the present system is operated is stored. The annotation-added medical-care record 103 is one in which the clinical information that is available after the present system is operated is stored. Therefore, the clinical information DB 102 and the annotation-added medical-care record 103 may be managed as the same databases.

Referring back to FIG. 2, for constitution for preparation processing, the terminal apparatus 3 includes a background information pre-acquisition unit 301, a clinical information pre-acquisition unit 303, an annotation-added medical-term statistic extraction unit 305, a medical-term dictionary 306, and a standard code master directory 307. The background information pre-acquisition unit 301 has a function in which the background information in a prescribed range that is narrowed down by providing a period of time or other conditions is received from the background information DB 101 of the storage device 1 and background information 302 is generated. The clinical information pre-acquisition unit 303 has a function in which the clinical information in a prescribed range that is narrowed down by providing a period of time or other conditions is received from the clinical information DB 102 of the storage device 1 and clinical information 304 is generated. Data structures of the background information 302 and the clinical information 304 are the same as those of the background information DB 101 and the clinical information DB 102.

The annotation-added medical-term statistic extraction unit 305 has a function in which a co-occurrence statistical value (a statistical value of the probability that two terms will appear in close proximity) is calculated for a term that is included in the background information 302 and the clinical information 304, and in which an annotation-added medical-care term statistic 308, to which an interpretation and the like that appears in the medical-term dictionary 306 and the standard code master directory 307 are added as annotations, is generated. In FIG. 3, an explanation that corresponds to a term is included in the medical-term dictionary 306. A standard code or explanation that corresponds to a term is included in the standard code master directory 307. The term, the annotation, and the co-occurrence statistical value (the co-occurrence statistical value for the term and another term) are included in the annotation-added medical-care term statistic 308. Moreover, the co-occurrence statistical value for two terms may be managed with different data structures.

Referring back to FIG. 2, for constitution for processing at the time of creating the medical-care record, the terminal apparatus 3 includes an annotation-added term selection candidate generation unit 309, a feedback presentation unit 321, a feedback input unit 322, an annotation-added medical-care record text generation unit 323. The annotation-added term selection candidate generation unit 309 includes an input-in-process data acquisition unit 310, a term interpretation processing unit 312, an input-in-process background information acquisition unit 313, an input-in-process patient clinical information acquisition unit 315, a matching processing unit 317, and a score calculation and sorting processing unit 318. Moreover, although a constitution for inputting the electronic clinical record and the like is not illustrated, when it comes to the input of the electronic clinical record and the like, text data that is the medical-care record is input after a target patient, a person who performs inputting, such as a doctor, facilities where the inputting is performed, an input-target document classification, and the like are specified. In some cases, an image and the like are attached to the medical-care record.

The annotation-added term selection candidate generation unit 309 has a function in which an annotation-added word selection candidate list 320 that lists a plurality of selection candidates for a term of which the meaning is not specified is generated at the time of the input of the medical-care record by a person such as a doctor. Moreover, the time of the input has both of the meaning of a point in time at which the character string is input, and the meaning of a point in time at which input of a sequence of character strings is completed, and may denote any one of the points in time. The input-in-process data acquisition unit 310 has a function in which data of which the input by a person such as a doctor is in process is acquired as an input-in-process data 311. The term interpretation processing unit 312 has a function in which the input-in-process data 311 is parsed based on a part of speech, and a corresponding interpretation or standard code is acquired with reference to the medical-term dictionary 306 and the standard code master directory 307. Furthermore, the term interpretation processing unit 312 has also a function in which, in a case where a term that is extracted by performing the parsing based on the part of speech is not present in the medical-term dictionary 306 or the standard code master directory 307, such a term is added as a medical term (a newly-added term) 319, to the medical-term dictionary 306. A data structure of the medical term (the newly-added term) 319 is the same as that of the medical-term dictionary 306, but does not include the interpretation. Because of this, the person who performs the inputting can be requested to perform interpretation inputting, and can perform configuration in such a manner that associated background information or clinical information is configured as an interpretation.

The input-in-process background information acquisition unit 313 has a function in which the related background information is acquired as background information 314 from the background information DB 101 of the storage device 1 based on the patient ID, the user ID, the facilities ID, the document classification ID, or the like that is included in the biographical information which corresponds to the medical-care record that is created by a person such as a doctor. A data structure of the background information 314 is the same as that of the background information DB 101. The input-in-process patient clinical information acquisition unit 315 has a function in which the related clinical information is acquired as clinical information 316 from the clinical information DB 102 of the storage device 1 based on the patient ID or the like that is included in the biographical information which corresponds to the medical-care record that is created by a person such as a doctor. A data structure of the clinical information 316 is the same as that of the clinical information DB 102.

The matching processing unit 317 has a function in which, in a case where a plurality of candidates for the term that is extracted by the term interpretation processing unit 312 are present, term matching between information, such as the medical-term dictionary 306 and, the background information 314 or the clinical information 316, is performed on each candidate and in which the resulting consistence state (no consistence, partial consistence, or complete consistence, or the like) is obtained. The score calculation and sorting processing unit 318 has a function in which weighting is performed on the consistency state, a created state of a co-occurrence statistic (a state indicating whether the co-occurrence statistic is created without the annotation or is created with the annotation), or the like, and thus a score is calculated, based on the result of the matching by the matching processing unit 317 and on the co-occurrence statistical value for terms of the annotation-added medical-care term statistic 308, and in which sorting is performed in order of decreasing score and thus the annotation-added word selection candidate list 320 is generated.

The feedback presentation unit 321 has a function in which, in a case where a plurality of candidates of which the scores do not exceed a prescribed threshold remain ranked high in the annotation-added word selection candidate list 320, the person who performs the inputting is requested to make a selection of the right one from among the plurality of candidates and the selection is made through the feedback input unit 322. Furthermore, the feedback presentation unit 321 has also a function in which an annotation-added learning supervised data 325 is generated as information for updating the annotation-added medical-care term statistic 308. As illustrated in FIG. 3, the fields, that is, term, annotation, term candidate, and adoption or rejection (a result of the selection by the user) are included in the annotation-added learning supervised data 325. Contents of the annotation-added learning supervised data 325 are added, for accumulation, to an annotation-added learning supervised data 326 that is previously generated.

Referring back to FIG. 2, the annotation-added medical-care record text generation unit 323 has a function in which an annotation on the candidate that is automatically determined from the score, or an annotation-added medical-care record text 324 that includes an annotation on the candidate which is selected by the person who performs the inputting is generated. The annotation-added medical-care record text 324 is stored as the annotation-added medical-care record 103 of the storage device 1.

Furthermore, for constitution for updating the annotation-added medical-care term statistic 308, the terminal apparatus 3 includes an annotation-added medical-care term statistic update unit 327. The annotation-added medical-care term statistic update unit 327 has a function in which contents of the annotation-added medical-care term statistic 308 are updated based on the annotation-added medical-care term statistic 308 and the annotation-added learning supervised data 326.

Figure 4:
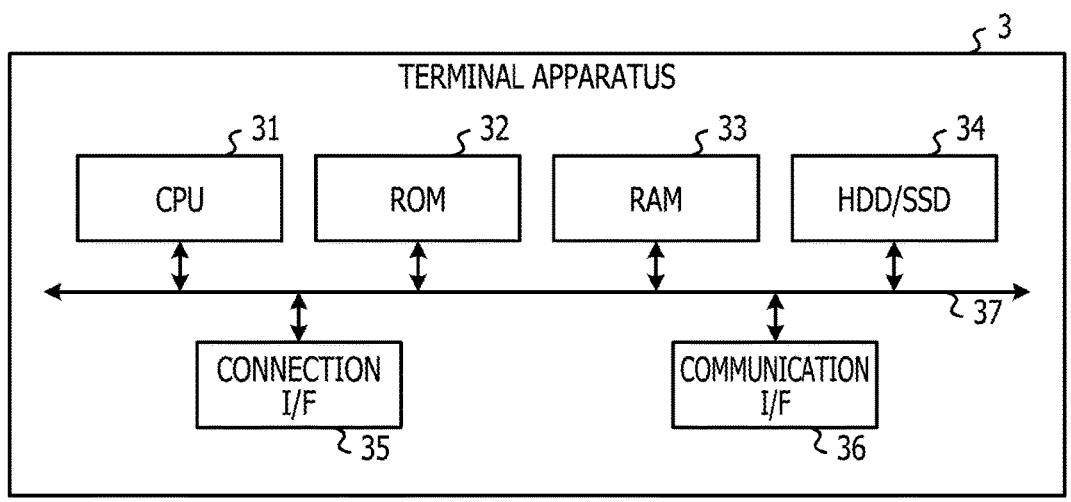
FIG. 4 is a diagram illustrating an example of a hardware constitution of a terminal apparatus.

FIG. 4 is a diagram illustrating an example of a hardware constitution of the terminal apparatus 3. In FIG. 4, the terminal apparatus 3 includes a central processing unit (CPU) 31, a read only memory (ROM) 32, a random access memory (RAM) 33, a hard disk drive (HDD)/solid state drive (SSD) 34, a connection interface (I/F) 35, and a communication I/F 36, which are connected to one another through a bus 37. The CPU 31 generally controls operation of the terminal apparatus 3 by executing a program that is stored in the ROM 32, the HDD/SSD 34, or the like with the RAM 33 as a work area. The connection I/F 35 is an interface to an apparatus that is connected to the terminal apparatus 3. The communication I/F 36 is an interface for perform communication with a different information processing apparatus through a network.

A function of the terminal apparatus 3 that is described referring to FIG. 2 is realized by the CPU 31 executing a prescribed program. The program may be acquired through a recording medium, may be acquired through a network, and may be built into the ROM.

Operation

FIGS. 5A and 5B are flowcharts each illustrating an example of processing according the embodiment described above. FIG. 5A illustrates an example of the processing at a preparation stage. FIG. 5B illustrates an example of the processing at the time of creating the medical-care record.

First, as illustrated in FIG. 5A, when starting the processing at the preparation stage, the background information pre-acquisition unit 301 receives the background information in a prescribed range that is narrowed down by providing a period of time or other conditions, from the background information DB 101 of the storage device 1, and generates the background information 302 (Step S11).

Next, the clinical information pre-acquisition unit 303 generates receives the clinical information in a prescribed range that is narrowed down by a period of time or other conditions, from the clinical information DB 102 of the storage device 1, and generates clinical information 304 (Step S12).

Next, the annotation-added medical-term statistic extraction unit 305 sets the background information 302 and the clinical information 304 to be inputs, and parses each of the background information 302 and the clinical information 304 by performing natural language processing such as morphological analysis (Step S13).

Next, with an N-gram interpretation, the annotation-added medical-term statistic extraction unit 305 calculates the co-occurrence statistical value (the statistical value of the probability that two terms will appear in close proximity) for a term that results from parsing the background information 302 and the clinical information 304 based on the part of speech (Step S14).

Next, if the term that results from parsing the background information 302 and the clinical information 304 based on the part of speech is a term that is present in the medical-term dictionary 306 and the standard code master directory 307 that is referred to, the annotation-added medical-term statistic extraction unit 305 adds an interpretation or a standard code that appears in the medical-term dictionary 306 and the standard code master directory 307, as an annotation on the term that results from the parsing (Step S15). Furthermore, the background information on the term that results for the parsing is also added to the annotation.

Then, the annotation-added medical-care term statistic 308 that includes the term, the annotation, and the co-occurrence statistical value is generated (Step S16), and the processing for prior preparation is ended.

Next, in FIG. 5B, when starting the processing at the time of creating the medical-care record, the input-in-process data acquisition unit 310 of the annotation-added term selection candidate generation unit 309 of the terminal apparatus 3 acquires text data of an article in a clinical record, of which the input by a person such as a doctor is in progress, as the input-in-process data 311 (Step S201). FIG. 6A illustrates an example of the input-in-process data 311 that is acquired.

Next, referring back to FIG. 5B, with the morphological analysis or the like, the term interpretation processing unit 312 parses the input-in-process data 311 based on the part of speech (Step S202). FIG. 6B illustrates "ASD" that is one term which is extracted from the input-in-process data 311 in FIG. 6A by performing the parsing based on the part of speech. In this example, it is assumed that the person who performs the inputting, such as a doctor, uses "ASD" to mean "Aortic Septal Defect".

Next, referring back to FIG. 5B, the term interpretation processing unit 312 acquires an explanation or a standard code for each term that is extracted, with reference to the medical-term dictionary 306 and the standard code master directory 307 (Step S203). At this time, in the case of a term that is not present in the medical-term dictionary 306 or the standard code master directory 307, such a term is added, as a medical term (a newly-added term) 319, to the medical-term dictionary 306 (Step S204). Moreover, the medical term (the newly-added term) 319 is added to the existing medical-term dictionary 306, in a state where a classification with which the medical term 319 can be identified as a new term is attached to the medical term 319.

FIG. 6C illustrates an example of the interpretation or the standard code for the term "ASD" in FIG. 6B, which is obtained with reference to the medical-term dictionary 306 and the standard code master directory 307. In this example, there are four different candidates for the term "ASD".

Next, referring back to FIG. 5B, in a case where a plurality of candidates for each term that is extracted in the term interpretation processing unit 312, which are associated with the medical-term dictionary 306 and the standard code master directory 307, are present, the input-in-process patient clinical information acquisition unit 315 extracts related clinical information 316 from the clinical information DB 102 based on the patient ID of a target patient and the like in the article in the clinical record, of which the input is currently in process (Step S205).

In the same manner, in the case where a plurality of candidates for each term that is extracted in the term interpretation processing unit 312, which are associated with the medical-term dictionary 306 and the standard code master directory 307, are present, the input-in-process background information acquisition unit 313 acquires related background information 314 from the background information DB 101 based on the patient ID of a target patient, the user ID of a user, the facilities ID of facilities, the document classification ID of a document, and the like in the article in the clinical record, of which the input is currently in process (Step S206). Moreover, the acquisition of the background information may be performed earlier than the acquisition of the clinical information, and may be performed concurrently with the acquisition of the clinical information.

FIG. 7A illustrates an example of the related clinical information 316 that is acquired by the input-in-process patient clinical information acquisition unit 315. FIG. 7B illustrates an example of the related background information 314 that is acquired by input-in-process background information acquisition unit 313.

Next, referring back to FIG. 5B, in the case where a plurality of candidates for each term that is extracted in the term interpretation processing unit 312, which are associated with the medical-term dictionary 306 and the standard code master directory 307, are present, the matching processing unit 317 performs associating (matching) of stated contents of the clinical information 316 and stated contents of the background information 314, with statements, such as the explanation of each term, and outputs a result of comparison, such as no consistency, partial consistency, or complete consistence (Step S207). FIG. 8 illustrates an example of the result of the matching with the clinical information (extraction data #2) in FIG. 7A and the background information (extraction data #3) in FIG. 7B for each of the four candidates that are extraction data #1 in FIG. 6C. That is, for the first candidate and the second candidate, there is not consistence with the clinical information and the background information. Furthermore, for the third candidate, partial consistence and complete consistence are present. For the fourth candidate, partial consistence is present.

Next, referring back to FIG. 5B, the score calculation and sorting processing unit 318 calculates a score for a term for which a plurality of candidates are present, using the result of the comparison, the co-occurrence statistical value of the annotation-added medical-care term statistic 308, performs the sorting in order of decreasing score, and outputs the annotation-added word selection candidate list 320 (Step S208).

Because the annotation-added medical-care term statistic 308 is based on pieces of document data of the background information DB 101 and the clinical information DB 102 that do not limit a data input environment, and is information on the probability that the character string will appear in these piece of document data, a common character string in the course of performing the matching and the scoring can be detected.

FIG. 9 illustrates an example of the co-occurrence statistical value of the annotation-added medical-care term statistic 308, and illustrates an example of the value in cases where the annotation is absent and is present. FIG. 10A illustrates an example of the calculated score (a numerical value in the head indicates the score) for the four candidates in FIG. 6C. In the example here, the weighting for no consistency is set to "0", the weighting for partial consistency is set to "0.3", the weighting for complete consistency is set to "1.0", and in the cases where the annotation is absent and is present, a calculation is made as 1:1. FIG. 10B illustrates an example in which the results in FIG. 10A are sorted in order of decreasing score.

Next, referring back to FIG. 5B, in a case where a specific condition is met, such as in a case where a plurality of candidates meet conditions such as the condition that a score is equal to or greater than prescribed value, with the feedback input unit 322, the feedback presentation unit 321 requests the person who performs the inputting to make a selection of the right one from among the plurality of candidates, and causes the selection to be made (Step S209). Moreover, in a case where a plurality of choices are present and where the person who performs the inputting is caused to perform checking of a candidate (a standard code, a standard name, or the like on the corresponding standard code master) that is automatically determined on the system side, with a GUI such as a hovering window, the checking can be simply performed instead of making the selection.

FIG. 11A illustrates a state where in a case where a plurality of candidates for term "ASD" in the fourth row from the top are present in the input-in-process data 311 in FIG. 6A, highlighting (a change in color, an underline, a change in font, a change in character style, or the like) is performed on the corresponding portion. As illustrated in this state in FIG. 11B, by superimposing a mouse pointer on a portion of the term "ASD", the hovering window that includes a plurality of choices (which is displayed in order of decreasing score) can be displayed and the selection of the right candidate can be made. The choice with the highest score is displayed in a state of being selected in advance, and thus only checking can be set to be performed.

Moreover, the selection of the right candidate from among the plurality of candidates is equivalent to selection of attribute information or classification information on a target term.

Next, referring back to FIG. 5B, the annotation-added medical-care record text generation unit 323 acquires annotation-added term information that includes learning information (the selection or the checking by the person who performs the inputting) from the feedback presentation unit 321, and outputs the acquired annotation-added term information to the annotation-added medical-care record text generation unit 323 (Step S210). The annotation-added medical-care record text 324 is stored as the annotation-added medical-care record 103 of the storage device 1. By retaining the annotation-added medical-care record text generation unit 323 in the storage device 1, since its generation, a text article in the electronic clinical record retains the annotation that is associated with a thesaurus or the standard code, and it is possible that high-precision data is used when it comes to the reuse of clinical data.

FIGS. 12A, 12B, and 12C are diagrams each illustrating an example of annotation information in the XML format. FIG. 12A illustrates an example that the annotation information is inserted into the head or rear of the article in the clinical record and illustrates that the term "ASD" is a standard medical term and means "Aortic Septal Defect". FIG. 12B illustrates that an expression is simplified by defining a tag in advance. FIG. 12C illustrates an example in which the annotation information is inserted into a portion in which the term "ASD" appears in the article in the clinical record. The expression in FIG. 12B is used, but the expression in FIG. 12A may be used. Furthermore, the annotation can include not only information indicating the meaning of a term, but also the attribute information, such as a medical-care department, that is included in the background information.

Referring back to FIG. 5B, the feedback presentation unit 321 generates the annotation-added learning supervised data 325 as information for updating the annotation-added medical-care term statistic 308 (Step S211). The annotation-added learning supervised data 325 is added to the annotation-added learning supervised data 326 for accumulation. Then, the annotation-added medical-care term statistic update unit 327 updates the contents of the annotation-added medical-care term statistic 308 based on the annotation-added medical-care term statistic 308 and the annotation-added learning supervised data 326. That is, based on feedback of the right candidate from the person who performs the inputting, learning (relearning) is performed and the annotation-added medical-care term statistic 308 is updated. Accordingly, the precision of the score calculation can be automatically increased through the operation.

Moreover, the example is described in which the annotation-added medical-care term statistic 308 is generated in an initial state based on pieces of information of the background information DB 101 and the clinical information DB 102 and where thereafter, the learning (the relearning) according to the input of the medical-care record is performed. However, the learning (the relearning) can be omitted by regenerating the annotation-added medical-care term statistic 308 from information that results from adding the annotation-added medical-care record 103 to the background information DB 101 and the clinical information DB 102 with a prescribed frequency.

Wrap-Up

As described above, according to the present embodiment, the meaning of the character string to be registered can be made definite.

The description is provided above according to the suitable embodiment is described above. The description is provided here with the specific examples being illustrated, but it is apparent that various amendments and changes to the specific examples can be made within the range that does not depart from the broad gist and scope that are defined in claims. That is, the details of the specific examples and the accompanying drawings do not impose any limitation on the interpretation.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment of the present invention has been described in detail, it should be understood that the various changes, substitutions, and alterations could be made hereto without departing from the spirit and scope of the invention.

What is claimed is:

1. A method that is executed by a computer, the method comprising:
   accepting an input of text from an input device;
   detecting a string of characters from the text, the string of characters corresponding to an abbreviation, the abbreviation corresponding to a plurality of phrases, the plurality of phrases having different meanings respectively;
   acquiring record information that indicates a record corresponding to an identifier related to the text and background information that indicates an attribute of the identifier;
   generating the plurality of phrases for display on an interactive display window of a display device, the plurality of phrases being generated from a database storing correspondence information including the string of characters, the plurality of phrases, and a co-occurrence statistical value calculated for each of the plurality of phrases, the co-occurrence statistical value indicating probability of appearance in the record information and the background information;

displaying the plurality of phrases on the interactive display window as candidates for an appropriate phrase corresponding to the abbreviation in the text, the interactive display window being configured to enable a user to select the appropriate phrase from among the plurality of phrases;

updating the correspondence information when the appropriate phrase is selected;

when an input of another text from the input device and the string of characters is detected from the another text, displaying the candidates determined based on the updated correspondence information;

recalculating the co-occurrence statistical value based on the updated correspondence information; and updating the database based on the recalculated co-occurrence statistical value.

2. The method according to claim 1, the method further comprising:

determining a display order of the plurality of phrases in the interactive display window based on the calculated statistical values.

3. The method according to claim 2, wherein the determining of the display order comprises:

identifying attribute of the text based on at least one of a user attribute related to a user who inputs the text, a target attribute related to a target which is described in the text, a facility attribute of a facility where the text is input, and an inputting environment attribute of an environment which indicates a type of the text;

comparing the attribute of the text with each of the related words of each of the plurality of phrases; and determining the display order of the plurality of phrases in the interactive display window based on a comparison result and the statistical values.

4. The method according to claim 1, wherein the detecting of the string of characters comprises continuously and automatically detecting the text for strings of characters during the input of texts.

5. The method according to claim 1, wherein the detecting of the string of characters comprises activating each string of characters in the text that corresponds to a plurality of phrases.

6. An information processing apparatus comprising:

a memory; and a processor coupled to the memory and configured to:
accept an input of text from an input device,
detect a string of characters from the text, the string of characters corresponding to an abbreviation, the abbreviation corresponding to a plurality of phrases, the plurality of phrases having different meanings respectively,
acquire record information that indicates a record corresponding to an identifier related to the text and background information that indicates an attribute to the identifier,
generate the plurality of phrases for display on an interactive display window of a display device, the plurality of phrases being acquired form the memory storing correspondence information including the string of characters, the plurality of phrases, and a co-occurrence statistical value calculated for each of the plurality of phrases, the co-occurrence statistical value indicating probability of appearance in the record information and the background information,
display the plurality of phrases on the interactive display window as candidates for an appropriate phrase corresponding to the abbreviation in the text, the interactive display window being configured to enable a user to select the appropriate phrase from among the plurality of phrases,
update the correspondence information when the appropriate phrase is selected,
when an input of another text from the input device and the string of characters is detected from another text, display candidates determined based on the updated correspondence information,
recalculate the co-occurrence statistical value based on the updated correspondence information, and
update the database based on the recalculated co-occurrence statistical value.

7. The information processing apparatus according to claim 6, wherein the processor is configured to determine a display order of the plurality of phrases in the interactive display window based on the calculated statistical values.

8. The information processing apparatus according to claim 7, wherein the processor is configured to:

identify attribute of the text based on at least one of a user attribute related to a user who inputs the text, a target attribute related to a target which is described in the text, a facility attribute of a facility where the text is input, and an inputting environment attribute of an environment which indicates a type of the text, compare the attribute of the text with each of the related words of each of the plurality of phrases, and determine the display order of the plurality of phrases in the interactive display window based on a comparison result and the statistical values.

9. The information processing apparatus according to claim 6, wherein the string of characters is detected by continuously and automatically detecting the text for strings of characters during the input of texts.

10. The information processing apparatus according to claim 6, wherein the processor is configured to activate each string of characters in the text that corresponds to a plurality of phrases.

11. A non-transitory computer-readable medium storing a program that causes a computer to execute a process, the process comprising:

accepting an input of text from an input device;

detecting a string of characters from the text, the string of characters corresponding to an abbreviation, the abbreviation corresponding to a plurality of phrases, the plurality of phrases having different meanings respectively;

acquiring record information that indicates a record corresponding to an identifier related to the text and background information that indicates an attribute to the identifier;

generating the plurality of phrases for display on an interactive display window of a display device, the plurality of phrases being generated from a database storing correspondence information including the string of characters, the plurality of phrases, and a co-occurrence statistical value calculated for each of the plurality of phrases, the co-occurrence statistical value indicating probability of appearance in the record information and the background information;

displaying the plurality of phrases on the interactive display window as candidates for an appropriate phrase corresponding to the abbreviation in the text, the interactive display window being configured to enable a user to select the appropriate phrase from among the plurality of phrases;

updating the correspondence information when the appropriate phrase is selected;

when an input of another text from the input device and the string of characters is detected from the another text, displaying the candidates determined based on the updated correspondence information;

recalculating the co-occurrence statistical value based on the updated correspondence information; and updating the database based on the recalculated co-occurrence statistical value.

12. The non-transitory computer-readable medium according to claim 11, process further comprising:

determining a display order of the plurality of phrases in the interactive display window based on the calculated statistical values.

13. The non-transitory computer-readable medium according to claim 12, wherein the determining of the display order comprises:

identifying attribute of the text based on at least one of a user attribute related to a user who inputs the text, a target attribute related to a target which is described in the text, a facility attribute of a facility where the text is input, and an inputting environment attribute of an environment which indicates a type of the text;

comparing the attribute of the text with each of the related words of each of the plurality of phrases; and determining the display order of the plurality of phrases in the interactive display window based on a comparison result and the statistical values.

14. The non-transitory computer-readable medium according to claim 11, wherein the detecting of the string of characters comprises continuously and automatically detecting the text for strings of characters during the input of texts.

15. The non-transitory computer-readable medium according to claim 11, wherein the detecting of the string of characters comprises activating each string of characters in the text that corresponds to a plurality of phrases.

* * * * *